United States Patent
Olek et al.

(10) Patent No.: US 11,725,243 B2
(45) Date of Patent: Aug. 15, 2023

(54) EPIGENETIC METHOD FOR THE IDENTIFICATION OF FOLLICULAR T-HELPER-(TFH-) CELLS

(71) Applicant: Precision for Medicine GmbH, Berlin (DE)

(72) Inventors: Sven Olek, Berlin (DE); Ulrich Hoffmüller, Berlin (DE)

(73) Assignee: Precision for Medicine GmbH, Berlin (DE)

( * ) Notice: Subject to any disclaimer, the term of this patent is extended or adjusted under 35 U.S.C. 154(b) by 364 days.

(21) Appl. No.: 15/526,632

(22) PCT Filed: Dec. 4, 2015

(86) PCT No.: PCT/EP2015/078725
§ 371 (c)(1),
(2) Date: May 12, 2017

(87) PCT Pub. No.: WO2016/087663
PCT Pub. Date: Jun. 9, 2016

(65) Prior Publication Data
US 2019/0100800 A1    Apr. 4, 2019

(30) Foreign Application Priority Data

Dec. 5, 2014 (EP) .................................... 14196613

(51) Int. Cl.
*C12Q 1/6881* (2018.01)
*C12Q 1/6886* (2018.01)
*C12Q 1/6883* (2018.01)

(52) U.S. Cl.
CPC ......... *C12Q 1/6881* (2013.01); *C12Q 1/6883* (2013.01); *C12Q 1/6886* (2013.01); *C12Q 2600/106* (2013.01); *C12Q 2600/118* (2013.01); *C12Q 2600/154* (2013.01); *C12Q 2600/156* (2013.01); *C12Q 2600/158* (2013.01)

(58) Field of Classification Search
CPC combination set(s) only.
See application file for complete search history.

(56) References Cited

U.S. PATENT DOCUMENTS

| | | | |
|---|---|---|---|
| 2007/0269823 A1* | 11/2007 | Huehn | C12Q 1/6886 435/6.16 |
| 2011/0028333 A1* | 2/2011 | Christensen | G16B 20/20 506/8 |
| 2011/0136114 A1* | 6/2011 | Case | C12N 5/0618 435/6.11 |

FOREIGN PATENT DOCUMENTS

| | | |
|---|---|---|
| EP | 2141245 A1 | 1/2010 |
| EP | 2639305 A1 | 9/2013 |
| WO | WO 2013/135454 A1 | 9/2013 |

OTHER PUBLICATIONS

Stahl (The Journal of Biological Chemistry (1990) vol. 265, pp. 8833-8841).*
Zhang (PLOS Genetics (2009) vol. 5, e1000438).*
Sabbioni et al (Mol Diagn 7(3):201-207 [2003]).*
Ushijima (Nature Reviews. 2005. 5: 223-231).*
Brooks et al ( Cancers Causes control (2009) vol. 20, pp. 1539-1550).*
Walsh et al teaches (Genes & Development (1999) vol. 13, pp. 26-36).*
Ehrlich et al. (2002 Oncogene vol. 21 p. 5400).*
Benner et al (Trends in Genetics (2001) vol. 17, pp. 414-418).*
May et al (Science (1988) vol. 241, p. 1441).*
"Non-follicular T-cells" (https://scholar.google.com/scholar?q=%22non-follicular++t+cell%22&hl=en&as_sdt=0%2C47&as_ylo=&as_yhi=2014, Nov. 11, 2020).*
Schmidl (Genome Research )2009) vol. 19, pp. 1165-1174).*
Okhura (Immunity (2013) vol. 38, pp. 414-423).*
Metcalfe (Gens and Immunity (2011) vol. 12, pp. 157-168).*
Shin (Mol Cells (2011) vol. 37, pp. 181-189).*
Chtanova (J Immunol 2004; 173:68-78).*
De Leval ( Blood. 2007;109:4952-4963).*
Hirahara (Immunology (2011) vol. 13, pp. 235-245).*
Ahearne, M.J. et al., "Follicular Helper T-cells: Expanding Roles in T-cell Lymphoma and Targets for Treatment." *British Journal of Haematology*, May 2014, 166:326-335, doi: 10.1111/bjh.12941.
Baron, U. et al., "DNA Demethylation in the Human FOXP3 Locus Discriminates Regulatory T Cells from Activated FOXP3⁺ Conventional T Cells." *Eur. J. Immonul.*, Aug. 2007, 37:2378-2389, doi: 10.1002/eji.200737594.
Database Geneseq [Online], "Human Leukemia Inhibitory Factor (LIF) Gene Exon 2 Amplicon, Seq ID 6." May 2014, retrieved from EBI accession No. GSN:BBC46035, Database accession No. BBC46035, the whole document.
Hale, J.S. et al., "Distinct Memory CD4⁺ T Cells with Commitment to T Follicular Helper- and T Helper 1-Cell Lineages are Generated after Acute Viral Infection." *Immunity*, Apr. 2013, 38:805-817, doi: 10.1016/j.immuni.2013.02.020.

(Continued)

*Primary Examiner* — Steven Pohnert
(74) *Attorney, Agent, or Firm* — BakerHostetler (57) ABSTRACT

The present invention relates to a method, in particular an in vitro method, for identifying follicular helper T cells, comprising analyzing the methylation status of at least one CpG position in the mammalian gene region for leukemia inhibitory factor (LIF), wherein a demethylation of said gene region is indicative for a follicular helper T cell, when compared to a non-follicular helper T cell. The analyses according to the invention can identify follicular helper T cells on an epigenetic level and distinguish them from all other cells in complex samples, such as, for example, other blood cells. The present invention furthermore provides an improved method for quantifying follicular helper T cells in complex samples. The method can be performed without a step of purifying and/or enriching cells, preferably in whole blood and/or non-trypsinized tissue.

18 Claims, 4 Drawing Sheets
Specification includes a Sequence Listing.

(56) References Cited

OTHER PUBLICATIONS

Kašpar, P. et al., "Identification of CpG Island at the 5' End of Murine Leukemia Inhibitory Factor Gene." *FEBS Letters*, Mar. 1993, 319(1-2):159-162, doi: 10.1016/0014-5793(93)80058-3.

Shin, J.E. et al., "Epigenetic Up-Regulation of Leukemia Inhibitory Factor (LIF) Gene During the Progression to Breast Cancer." *Mol. Cells*, Feb. 2011, 31:181-189, doi: 10.1007/S10059-011-0020-z.

Stahl, J. et al., "Structural Organization of the Genes for Murine and Human Leukemia Inhibitory Factor." *The Journal of Biological Chemistry*, May 1990, 265(15):8833-8841.

Zhang, X. et al., "Follicular Helper T Cells: New Insights Into Mechanisms of Autoimmune Diseases." *The Ochesner Journal*, Spring 2013, 13(1):131-139.

\* cited by examiner

CTGAGGATGGGTCCCATGGGGCCAAGTCCAGGCTGGGTGGGAGAGCGACTCAGAGCCAGGGCCGCAAGGTGGGCCTGGCA
CAGAGCTCCCAAGTCCACAGGGAGATGAGGTGATGGGCGAGTCAGCCGGGCCCCCGGGTGGAATCAGCAACTCTGGTTTCC
AGACAAGTTTGTCTTTCTCGAAGCCCATCCTGGGGGAATGCAGCCAGCCCCAAGCTAAGCCGGATGAAGCAGGAAGGAGAAG
GCAGTCCCTGCATCCTGGACAAGGGTGAGTGTGGCCCACATCTCAACAGCCACATCCTCGTCTTGCTGTTGGGATGGACAGAT
GGACAACTCCGGGCCGCACCCTCCACCCCAACCCCAGGCCTCAGGACCTGCCTGCACACTGCCCACGCGCCATCCAGGTAAAG
TGCTTAGAGAGCGACAGGGAAAGGTGCAAAGTGAGTGAAAAGTACCATAATTAGTACCATCATCTTGTCGGAGGAACTTGGA
GGCCGGCAGCCCGCTCAGGGTTTGAGAAGAAGCCAGAACACTGCTCTGAGCAGCTGCCCCAACTCTGCTGCCTCCTTCCCTCC
CCTGCTCTCAGACTGGAGGGCGTTTCTCCACTCGCCTGGCCCCAGCACAAAGGAAGAGATCGGGTTCCCTGCCTGGGAGCCCA
GACATGGGTGGGAGTGGGATGGGGGTGGAGCAGGAGGGCCCACAGCTTCCTGGTCTGAGTCCCAGGCATCTGCAGCCTCCC
TCTCCTCCTCTTGGGAGCAATGGGCAGCTGATCCCCCAGTCTACCCCACCTTCCTGGGGTCTGGCCCAGCCAGGCCCCCCGCA
CCGTCTATGGGTGTCCGGGCCACAGGAGGAGCTTCCCTGCTGTGTCGGAGCATGCTGGGTGCAGGGGCAGGGTTGTTCCAGG
GCGCTATTTCAGAGGCAGCATGGGGACACAGAAACAAGGACAGGGTGGGCCACAAGGACTGTCTTGCCCACTGCTCCAGGG
GGCACAATATCTGCCAGGAACAGTGCGCCTCACAACACAATGCTGGGGCGCCCAAGAACAGTGTGAACCAGCCCCCTGGAAT
CAAGACAGAAAGGCACCCGGCCTCTCCACAAATTGGCCCAGCCCCTGCAGCCTGGACCCTGACACCCTAAAGCAAGTCACAGT
AGGGGATGGGGGGGGGTGGAGCAAGGCCCCCCACTCCCACTCAGGCCTCCCCATTCTCTCAGATCCGACCCTTCTCTGAGCTT
CACCCGTAAGGCTTATTCCACTTGTAACATTGTCGACTTCCAGACCAGGCCCTGCTAAGCCCTGGCCCTGGCGCTTGTGTCGGG
AGCCATCATCATATTTTGTTGAGTAGGGACCAGGGAAAGGGGAATTAACTTGGCCACTGAAAGCACCAATAAGTTAATATAAA
TAGGATATCATAATAAATAGAAATCATGCCAGGTCAGACGCACAGCACGCTTGGAGCTCAGGGTTCCCTGAGACCCTGACCCT
AAGTTCTGCTGTTCCCTTGCCCTGGGGACCAGAGACGGCCTCCAGTCCCCCTCAAGTACCTCTGTGTGACCTCACAAGGCCTCC
CAGGGCCTCAGATGTGAGCTGCTACTCTGAGCTACCCCAGCCCCTTCTTACAGACCTTTACCCAGAGGAAGAGCCTGGGTCCCT
CAGAACCTCTGCACCTGACTTAGCAACCTGCCCCTGCCCTACCCACCTCCACAAACCCCTGCTGCAGGTCCAGCCATCAGACCCT
GGCCATCCAGGCTGCAGGGAAGATCACGGGGAAGAGAACGAAGAACCTACCAAAGCTTTCCAGGCCTCTCCTCCTCCCAGT
GTCTTCCTTCCCAGGCCTGAAGGTGGCTTCTCTGCCTCCCCAAGAGCCTGAATGCCAAGTGACCTCCTTCTGGAAACTTCTGCCA
GATTGTTCCTATGCCCAAGTTCTCTGATCATCCTCAAAAGAAGACAGCCTTCCATCCCAGAGGCCCCTCTCTATCTTCCACTCATC
AAACTTCTAGGGGACAAGGAGTCCTTTGGGATCCTAGCCCCTCTGGCCCACCTAAGTCCCAACCTAAGGGGCAGCAAAGGCAC
AGATGGTGATAATTTGCTGGGGGCTGGTCCACTCCCTGGGCCCTGCTGTCTCACCCTGTGGTCAGGGCTCTTGTAGATGACTT
GTGTAGTTTGTTCACTGCACAAAGTGAGCAAGGGGCCAAAGGGACAAGTAGAGGCAGAAGTCCAGCCCACGCTCCCCAGTCC
ACAATCTCCCAGAGGAAGGGGCACCTTCTTCTAGCTCCCTCCCTATGGAAGTTTCCACTCTGCTCAGCTTCATCACAGCCCAGCC
CAGAGTGGAGTGGACTGGCCAGGCACCCTCGGGGTCTGCCAGCAGCCCCATTTGGGTTTAGCGATGCCCTGGGCCCCAGCC
ACCCTTGGACAGGCCCCCACATCTGGACCCAACTCCTGAGATCCCTCGGTTCACAGCACACTTCAAGACCTCCTGCTAGAAGG
CCTGGGCCAACACGGCGATGATCTGCTTATACTTCCCCAGGAGTTGACAGCCCAGCTTCTTCTTCTGGAAGACATCCTTACCC
GAGGTGTCAGGGCCGTAGGTCACGTCCACATGGCCCACGTGGTACTTGCTGCACAGGCGGCACAGCACGTTGCTAAGGAGG
CCTCGCAGGATGTCGGCGGTGGCGTTGAGCTTGCTGTGGAGGCTGAGGGCACTGGGGTTGAGGATCTTCTGGTCCGGGTG
ATGTTGCCCAGGGAGGTGCCAAGGTACACGACTATGCGGTACAGCTCCACCAGCTTGGCCTTCTCCGTGCCGTTGGCGTGGA
AGGGCGGGAAGTCCGTCACGTTGGGGCCACATAGCTTGTCCAGGTTGTTGGGGAACGGCTCCCCTGGGCTGTGTACTGAG
GGGCAGAAGGGAGGTGACGTGGGAGTCAGGGGTCAGTGTCCCAGCCCTGCCGCCAACCCTTTGGGCAAGCTCTTGCGTCTGT
TTCCCCATCTAGCCGCATGAGGACCCAACTCCTTGCCCTGTAAGCATCTGGAATTGTCATGAGAGCCAAAACTAATTGTAATGTG
AGTGCCCTTGCTAAAGATCAAAGACTGAGCCATGCACGCAGTCATCATTATCATCATCATCATCACCACCCTAAGGGGACA
GAAGGGAAAACTCGGTGTCTAGCCCTAGCTGGGGCACCACACACAAGTACTTCCATCCCTGCACTCACAATGTTCCGGGACGC
CCCTCCATGCCCAGCACCCACAGCCCACTGCCTCTCAACCGCATCTCCCTGGTGCCTCACGCCCATTTCCCCTCCATCCCTCGCTC
CCTGCAGCAGGACAATCACAAGATAAGAAGTGCCAGGTCCCCACCTTTGCACTCAGTTCTCCCCTTGCTAACTGGGCACCCTGG
GGAAGCTTCCCTGGGGAAGCTTGGGCAGGAAGTGGCGGGAGTCTGGGGGTGGTTTAATCAAGCCCTCTCCCCATTCTCTCCTT
CCAGCCCCAAAAGGTCCCCTCAACCCAGATCAGGACAGCCCCTAATGATATTTACAAGCCCCCTCCCTGCCATCTCCTGTCAGTA
TCCCAGGGGTAACTTACATAGAGAATAAAGAGGGCATTGGCACTGCCATTGAGCTGTGCCAGTTGGCTCCTGATCTGGTTCAT
GAGGTTGTTGTGACATGGGTGGCGTATGGCACAGGTGGCGTTGACAGGGGTGATGGGAGGGGGCTCCCCGCCCCATGTTT
CCAGTGCAGAACCAACAGCAGGGGCACAACTCCTGGGGACAGTCAGGAAGAAGCCATGAGTAGAAAGGCAGGAAAGGGTG
GCCTGGGGTCATGGCACACCGGATGGGGGTCCAACAATGGCCGCATGGGAGAGGACTCCTGGTTCCCCCTCACCACCTGCAG
CTGTCTTCCTGGGGCCTAGTCTTCACTCTGTCACTGCGTGTGTTTCTCTGTCTCCCTTTCTCTACCTTAGTTCTCCCTGCTCTCTTCT
GGGATGACGTAAAGATGAGGGCAAGACACAAGCCATTTCCACCCAAAGGGTGCAGGGTCCAGGAGAGACTCCCAGCCATCCC
ACCCTTTCCCTCAGGAAGGCAAAGGTCCTAAGGCCCCCTGGCCCTCTGGCTGGAAGGCACCAGGCCCCAGGCCCAGCAGGCA
CCAGGAGAAAGGAGACCCCTCTCTTCCCACCTCCCGTGGTGGCCCAGGTTCCTCAGCAGCGCTTCCCACTCACTGGCCCATTGC

FIG. 3 (continued)

```
AGCCCAAATCTCCGAAGCCAGGCACCCATGGGGGCCACGGGGCATGGGGGAGTGGGGAGGAGTCCTCGGTTGACCCTCATC
TCCCTCCCAAACCTGCCACTTGATTCTGGCTCCCTGGGCCAATTGCCCCCAATTCTGCCCCCGCCCCCATCATCCTCTATCTCTTC
CTTCCCTAGTGTCCCCTATCTCACTCAAGCTCACCCCATTTCTGCCTGGCTGTCCCCACTCTCCATCCCCAAATCATCATTCAAAAC
TCTCTGTTCCCCCAGCTCCGGACAGCCCCTGACTCCATGCCTTCTCCCGACTCATCCGCTGTCCCTTGTCCCAGGGGTTCCCCTCC
CTCCTAACACACACACACCGGCTCAGGGAGGGAGAGGAAATGGTGCACCAGGAGAGAGAAAAGGCAAAAGGTCATAGGCAG
TCGGGTGGGCGGGGAGGAAGGAAAGTGAAAGGTGACAGGAGAGCTGGGAGCTGTCCCGACATGTCCTGGTTTGCCCCTCCC
CCAGGGGGGCCTGTTCTCCCGACTCCCCCCAGGCCCCCTTAGACGCTTTTCCAGGGCTCTGCAGAAGGGCACCTGAAGATGGT
GGGGGCCGGGGTCAGCGGGCGAGTGAGGCTGGAGACCTCCCCCGGATCCCCCATGCTGGAACAGCGGGGACAGGGGCCTCC
TCAAGTTCACTTCTCCTGGGTCCCCTGTTCGTCCCAGCATCCCAAGGCAGTGCTGAGGCCCCGGGGTGGCTGCGGGAGGGGG
GCCACACCCCTATATCTCACCTAGCGCAGACCACACGCTTCCAGACACCAGCAGATGGAGGCGGCACCTGCTCCCGTCCCAGG
CCGGAGTTTGCAAGCTGCTCGCCGCCCGCGCCCCTCCCTGGGAGCAGCCCGGGACCGCGGTTGGAAAGGAGAAAGCGGAAA
GAAAGAAAGAAAAGAAAAAGAGAGAGGGAGAGTGAATCGGGAGAAAGCGCAGAGGGAAGAGCAGCCAGCGAGTGTCCG
GAGCGAGGAGGAGGAGGAGGAGAAGGAGAGGGGGAAGAAGAGGAGGAGGAGGAAGGCTCGGCGCCCCCTCCCTCGCCGC
CAACCTGCCGCGGGGCGTGCGGTGCTTGGGACCATGTGCCCGCGCTCGCTCCGGGCCGCCACCCAGCGCCTCCGGTGGCTGC
GCGGGCGCCCCAAGTGTTCGTGTGTCTGCGGCGGGTGGGCGTCCGGCTCGCGCTGCCAAGCGCCCCAAGTTGCCGCCGCGCC
CCGCAGCGGGGACGCGAAGCCGGCGCGGGGCGGGTGTATTTACCTGCCGCCAAGACCTTCATTATGG
```

EPIGENETIC METHOD FOR THE IDENTIFICATION OF FOLLICULAR T-HELPER-(TFH-) CELLS

CROSS REFERENCE TO A RELATED APPLICATION

This application is a National Stage Application of International Application Number PCT/EP2015/078725, filed Dec. 4, 2015; which claims priority to European Patent Application No. 14196613.5, filed Dec. 5, 2014; both of which are incorporated herein by reference in their entirety.

The Sequence Listing for this application is labeled "SeqList-16May17.txt", which was created on May 16, 2017, and is 9 KB. The entire content is incorporated herein by reference in its entirety.

The present invention relates to a method, in particular an in vitro method, for identifying follicular helper T cells, comprising analyzing the methylation status of at least one cytosine-phosphodiester-guanine (CpG) position in the mammalian gene region for leukemia inhibitory factor (LIF), wherein a demethylation of said gene region is indicative for a follicular helper T cell, when compared to a non-follicular helper T cell. The analyses according to the invention can identify follicular helper T cells on an epigenetic level and distinguish them from all other cells in complex samples, such as, for example, other blood cells. The present invention furthermore provides an improved method for quantifying follicular helper T cells in complex samples. The method can be performed without a step of purifying and/or enriching cells, preferably in whole blood and/or non-trypsinized tissue.

Furthermore, the present invention relates to a kit for performing the above methods as well as respective uses thereof. It is one aim of this invention to provide a novel, more robust means to quantitatively detect and measure follicular helper T cells of the blood within any solid organs or tissue or any body fluid of a mammal.

BACKGROUND OF THE INVENTION

T cell help to B cells is a fundamental aspect of adaptive immunity and the generation of immunological memory. Follicular B helper T cells (also known as just Follicular helper T cells or TFH), are antigen-experienced CD4+ T cells found in the periphery within B cell follicles of secondary lymphoid organs such as lymph nodes, spleens and Peyer's patches, and are commonly identified by their constitutive expression of the B cell follicle homing receptor CXCR5 (Fazilleau et al.; Mark, L; McHeyzer-Williams, L J; McHeyzer-Williams, M G (March 2009). "Follicular helper T cells: lineage and location". Immunity 30 (3): 324-35).

T(FH) cells depend on expression of the master regulator transcription factor Bcl6. Other distinguishing features of T(FH) cells are the expression of PD-1, SAP (SH2D1A), IL-21, and ICOS, among other molecules, and the absence of Blimp-1 (prdm1). T(FH) cells are important for the formation of germinal centers. Once germinal centers are formed, T(FH) cells are needed to maintain them and to regulate germinal center B cell differentiation into plasma cells and memory B cells.

Even though almost all cells in an individual contain the exact same complement of DNA code, higher organisms must impose and maintain different patterns of gene expression in the various types of tissue. Most gene regulation is transitory, depending on the current state of the cell and changes in external stimuli. Persistent regulation, on the other hand, is a primary role of epigenetics—heritable regulatory patterns that do not alter the basic genetic coding of the DNA. DNA methylation is the archetypical form of epigenetic regulation; it serves as the stable memory for cells and performs a crucial role in maintaining the long-term identity of various cell types. Recently, other forms of epigenetic regulation were discovered. In addition to the "fifth base" 5-methylcytosine (mC), a sixth (5-hydroxymethylcytosine, hmC), seventh (5-formylcytosine, fC) and eighth (5-carboxycytosine, cC) can be found (Michael J. Booth et al. Quantitative Sequencing of 5-Methylcytosine and 5-Hydroxymethylcytosine at Single-Base Resolution Science 18 May 2012, Vol. 336 no. 6083 pp. 934-937).

The primary target of mentioned DNA modifications is the two-nucleotide sequence Cytosine-Guanine (a 'CpG site'); within this context cytosine (C) can undergo a simple chemical modification to become formylated, methylated, hydroxymethylated, or carboxylated. In the human genome, the CG sequence is much rarer than expected, except in certain relatively dense clusters called 'CpG islands'. CpG islands are frequently associated with gene promoters, and it has been estimated that more than half of the human genes have CpG islands (Antequera and Bird, Proc Natl Acad Sci USA 90: 11995-9, 1993).

Aberrant methylation of DNA is frequently associated with the transformation from healthy to cancerous cells. Among the observed effects are genome-wide hypomethylation, increased methylation of tumor suppressor genes, and hypomethylation of many oncogenes (reviewed, for example, by Jones and Laird, Nature Genetics 21:163-167, 1999; Esteller, Oncogene 21:5427-5440, 2002; and Laird, Nature Reviews/Cancer 3:253-266, 2003). Methylation profiles have been recognized to be tumor specific (i.e., changes in the methylation pattern of particular genes or even individual CpGs are diagnostic of particular tumor types), and there is now an extensive collection of diagnostic markers for bladder, breast, colon, esophagus, stomach, liver, lung, and prostate cancers (summarized, for example, by Laird, Nature Reviews/Cancer 3:253-266, 2003).

For one of the recently described modification of cytosine, 5-hydroxymethylation, the utility of oxidative bisulfate sequencing to map and quantify 5hmC at CpG islands was shown (Michael J. Booth et al. Quantitative Sequencing of 5-Methylcytosine and 5-Hydroxymethylcytosine at Single-Base Resolution Science 18 May 2012, Vol. 336 no. 6083 pp. 934-937). High levels of 5hmC were found in CpG islands associated with transcriptional regulators and in long interspersed nuclear elements. It is suggested that these regions might undergo epigenetic reprogramming in embryonic stem cells.

Hale J S et al. (in: Distinct memory CD4+ T cells with commitment to T follicular helper- and T helper 1-cell lineages are generated after acute viral infection. Immunity. 2013 Apr. 18; 38(4):805-17) based on gene expression profiles, epigenetic studies, and phenotypic and functional analyses found that there are distinct memory CD4(+) T cell populations with commitment to either Tfh- or Th1-cell lineages. Epigenetic modifications of the granzyme B locus distinguished Tfh memory from Th1 memory CD4+ T cells.

Kashiwakuma et al. (in: B and T lymphocyte attenuator suppresses IL-21 production from follicular Th cells and subsequent humoral immune responses. J Immunol. 2010 Sep. 1; 185(5):2730-6) disclose that follicular Th (Tfh) cells, which are non-Th1, non-Th2 effector T cells that express CXCR5 and provide help for B cells to produce Ig, also express lymphocyte attenuator (BTLA).

WO 02/083162 describes a method to treat, inhibit or prevent immune-driven rejection of grafted tissue or cells in a recipient host by administering a pharmaceutically effective amount of CD8+ T cell inhibitory agent.

US 2012-0177597 discloses a method for promoting development of IL-21 producing T follicular helper cells (Tfh) in a subject from naive CD4.sup.+ T cells comprising the steps of: providing the one or more naive CD4.sup.+ T cells; contacting the one or more naive CD4+ T cells with a cytokine or a cytokine cocktail selected from: IL-6/TGF-b/IL-12; or IL-12; or TGF-b and IL-12; and differentiating the one or more naive CD4+ T cells into the one or more IL-21 producing Tfh cells.

In view of the above, it is an object of the present invention to provide an improved and in particular robust method based on DNA-methylation analysis as a superior tool in order to more conveniently and reliably detect, identify, discriminate, and quantify follicular helper T cells.

The present invention solves the above object by providing method for identifying follicular helper T cells in a sample, comprising analyzing the methylation status (bisulfite convertibility) of at least one CpG position in the mammalian gene region for leukemia inhibitory factor (LIF), wherein a demethylation of said gene region is indicative for a follicular helper T cell, when compared to a non-follicular helper T cell.

The protein leukemia inhibitory factor (LIF, or CDF; DIA; HILDA; MLPLI) has the capacity to induce terminal differentiation in leukemic cells. Its activities include the induction of hematopoietic differentiation in normal and myeloid leukemia cells, the induction of neuronal cell differentiation, and the stimulation of acute-phase protein synthesis in hepatocytes. The gene for human LIF is found on chromosome 22, NC_000022.11 (30240447 . . . 30257381, complement).

The present invention is further based on the surprising identification of a region of the LIF gene by the inventors, as specific epigenetic marker, allowing the identification of follicular helper T cells as well as the clinical routine application of said analysis.

In the context of the present invention, the genomic region according to SEQ ID NO: 5 allows the identification of follicular helper T cells. Surprisingly, the discriminatory pattern of bisulfite convertible and non-convertible cytosine is particularly and even exclusively limited to the genomic region according to SEQ ID NO: 5 and preferably the region according to SEQ ID NO: 1 for follicular helper T cells as shown using the amplicon according to SEQ ID NO: 1.

Preferably, the genomic region as analyzed in the present invention comprises the amplicon according to SEQ ID NO: 1, and optionally includes further about 100, 200, 300, 400, 500, 600, 700 800, 900, or 1000 bases, or even 1500 or 2000 bases to a maximum of about 2200 additional bases upstream of amplicon AMP2305, and/or optionally includes further about 100, 200, 300, 400, 500, 600, 700 800, 900, or 1000 bases, or even 1500, 2000 or 2500 bases to a maximum of about 2600 additional bases downstream. In other words, the length of the genomic region as analyzed comprising the amplicon AMP2305 (about 500 bases) can be about 600, 700, 800, 900, 1000, or 1500 bases up to about 5300 bases.

More preferred is the genomic region comprising the sequence of AMP2305, and furthermore the sequence including the three CpGs upstream thereof and 10 of the CpGs downstream thereof (as indicated in FIG. 3). More preferably, the genomic region downstream includes all CpGs as shown in FIG. 3.

"About" in the context of the present invention shall mean the indicated value +/−10%.

The inventors could demonstrate that in the follicular helper T cells the CpG motifs are almost completely demethylated (i.e. to more than 70%, preferably 80%, preferably, more than 90% and most preferred more than 95%), whereas the same motifs are completely methylated in all other immune cells.

The differential methylation of the CpG motifs within the aforementioned regions is a valuable tool to identify follicular helper T cells, such as will be required/or at least of some value for identifying and quantifying said cells in autoimmune diseases, transplant rejections, cancer, allergy, primary and secondary immunodeficiencies, such as, for example, HIV infections and AIDS, Graft versus Host (GvH), hematologic malignancies, rheumatoid arthritis, multiple sclerosis, or a cytotoxic T cell related immune status in any envisionable diagnostic context. The assay allows measurement of follicular helper T cells without purification or any staining procedures.

Another preferred aspect of the method according to the present invention then further comprises a quantification of the relative amount of follicular helper T cells based on comparing relative amounts of said methylation frequency in the region as analyzed with relative amounts of the methylation frequency in a control gene, such as, for example, GAPDH. Said quantification is thus achieved based on the ratio of the bisulfite convertible DNA to non-convertible DNA in the genetic region of LIF (e.g. of SEQ ID NO: 5 or SEQ ID NO: 1) as described and analyzed herein. Most preferred is a quantification of the relative amount of follicular helper T cells is based on an (preferably parallel or simultaneous) analysis of the relative amount of bisulfite convertible DNA of cell-specific region for LIF, and of the relative amount of bisulfite convertible DNA of cell-unspecific genes (preferably designated "control genes" or "control regions", such as, for example, the gene for GAPDH).

In a further preferred embodiment of the method according to the present invention, said analysis of bisulfite convertibility comprises amplification with at least one primer of suitable primer pairs that can be suitably designed based on SEQ ID NO: 5 or SEQ ID NO: 1, preferably oligomers according to any of SEQ ID NOs: 2 to 4.

In contrast to FACS and mRNA measurements, using the methods according to the present invention, the measurement(s) and analyses can be done independent of purification, storage—and to quite some extent—also to tissue quality.

Preferably, the amplification involves a polymerase enzyme, a PCR or chemical amplification reaction, or other amplification methods as known to the person of skill as described below, e.g. in the context of methylation-specific PCR (MSP), HEAVYMETHYL™, SCORPION™, methylation-sensitive single-nucleotide primer extension (MS-SN-UPE), METHYLLIGHT™, bisulfite sequencing, methyl specific restriction assays and/or digital PCR (see, for example Kristensen and Hansen PCR-Based Methods for Detecting Single-Locus DNA Methylation Biomarkers in Cancer Diagnostics, Prognostics, and Response to Treatment Clinical Chemistry 55:8 1471-1483 (2009)).

With the amplification, an amplicon of LIF gene region is produced that is a particularly preferred "tool" for performing the method(s) according to the present invention. Consequently, oligomers according to any of SEQ ID NOs: 2 to 4 or an amplicon as amplified by a primer pair based on SEQ ID NOs: 2 to 4 as mentioned above constitute preferred embodiments of the present invention. Thus, the sequences of SEQ ID NOs: 2 to 4 (and, if needed, the complementary sequences thereto) can be used to design primers for amplifications, i.e. serve as "beacons" in the sequence as relevant. Similarly, additional primers can be designed based on the amplicon according to SEQ ID NO: 1. Amplification can take place either in the genomic and/or bisulfite (i.e. "converted") DNA sequence.

The person of skill will furthermore be able to select specific subsets of CpG positions in order to minimize the amount of sites to be analyzed, for example at least one of CpG position selected from a CpG position in an amplicon according to SEQ ID NO: 1, and is preferably selected from CpG positions 1, 2, 3, 4, 5, 6, 7, 8, 9, 10, 11, 12, 13, 14, 15, 16, 17, 18, 19, 20, 21, 22, and 23 in the amplicon No. 2305 according to SEQ ID NO: 1. The positions are numerically counted from the 5'-end of an amplicon as generated and analyzed. Preferred are combinations of 3, 4, 5, 6, 7, 8, 9, or 10 positions, the analysis of which produces sufficient data and/or information in order to be informative in the context of the present invention.

The person of skill will furthermore be able to select specific subsets of CpG positions in order to minimize the amount of sites to be analyzed, for example at least one of CpG position 9, 10, 11, 12, 13, 14, 15, 16, 17, 18, 19, and/or 20 in the amplicon No. 2305 of the LIF specific bisulfite convertible region (SEQ ID NO: 1), or all sites as present on the bisulfite convertible region according to SEQ ID NO: 1.

In order to analyze the bisulfite convertibility of CpG positions, any known method to analyze DNA methylation can be used. In a preferred embodiment of the method according to the present invention, the analysis of the methylation status comprises a method selected from methylation specific enzymatic digests, bisulphite sequencing, analysis selected from promoter methylation, CpG island methylation, methylation-specific PCR (MSP), HEAVYMETHYL™, METHYLLIGHT™, methylation-sensitive single-nucleotide primer extension (MS-SNUPE), or other methods relying on a detection of amplified DNA. These methods are well known to the person of skill, and can be found in the respective literature.

In a preferred embodiment of the method according to the present invention, said method is suitable for routine application, for example on a DNA-chip. Based on the above information and the respective literature, the person of skill will be able to adjust the method as above to such settings.

In yet another preferred embodiment of the methods according to the present invention, said method is performed without a step of purifying and/or enriching said cells to be identified, preferably using whole blood and/or non-trypsinized tissue.

In another preferred embodiment of the method according to the present invention, the identification comprises a distinction of said follicular helper T cells from all major peripheral blood cell types and/or non-blood cells, preferably, but not limited to, from B-cells, cytotoxic T-cells, granulocytes, monocytes, NK-cells, and T-helper cells, and other cell types derived from other organs than blood.

In yet another preferred embodiment of the method according to the present invention, the sample is selected from a mammalian body fluid, including human blood samples, or a tissue, organ or a sample of leukocytes or a purified or separated fraction of such tissue, organ or leukocytes or a cell type sample. Preferably, said mammal is a mouse, rat, monkey or human. The samples can be suitably pooled, if required.

Another preferred aspect of the method according to the present invention then further comprises the step of concluding on the immune status of said mammal based on said follicular helper T cells. The follicular helper T cells can be quantified and be used as a benchmark to relatively quantify further detailed subpopulations (as but not limited to CD4, Th1, Th2, Th9, Th17, Th22, Treg), or it can be used as a predictive and/or screening and/or diagnostic and/or prognostic and/or adverse events detecting factor, or it can be used to finally detect this population to determine the overall immune activity status.

In yet another preferred embodiment of the methods according to the present invention, the mammal suffers from or is likely to suffer from autoimmune diseases, transplant rejections, infection diseases, cancer, and/or allergy as but not limited to *Trypanosoma cruzi*-infection, Malaria and HIV infection; Hematologic Malignancies as but not limited to chronic Myelogenous Leukemia, Multiple Myeloma, Non Hodgkin's Lymphoma, Hodgkin's Disease, chronic Lymphocytic Leukemia, Graft versus Host and Host versus Graft Disease, Mycosis fungoides, Extranodal T cell lymphoma, Cutaneous T cell lymphomas, Anaplastic large cell lymphoma, Angioimmunoblastic T cell lymphoma and other T-cell, B-cell and NK cell neoplasms, T cell deficiencies such as but not limited to lymphocytopenia, severe combined immunodeficiency (SCID), Omenn syndrome, Cartilage-hair hypoplasia, acquired immune deficiency syndrome (AIDS), and hereditary conditions such as DiGeorge syndrome (DGS), chromosomal breakage syndromes (CBSs), multiple sclerosis, rheumatoid arthritis, systemic lupus erythematosus, Sjögren's syndrome, systemic sclerosis, dermatomyositis, primary biliary cirrhosis, primary sclerosing cholangitis, ulcerative colitis, Crohn's disease, psoriasis, vitiligo, bullous pemphigoid, alopecia areata, idiopathic dilated cardiomyopathy, type 1 diabetes mellitus, Graves' disease, Hashimoto's thyroiditis, myasthenia gravis, IgA nephropathy, membranous nephropathy, and pernicious anemia; and B-cell and T-cell combined disorders such as but not limited to ataxia telangiectasia (AT) and Wiskott-Aldrich syndrome (WAS); and carcinomas such as but not limited to breast cancer, colorectal cancer, gastric cancer, pancreatic cancer, hepatocellular carcinoma, cholangiocarcinoma, melanoma, and head and neck cancer.

Another preferred aspect of the method according to the present invention then relates to a method as above, further comprising measuring and/or monitoring the amount of follicular helper T cells in response to chemical and/or biological substances that are provided to said mammal, i.e. in response to a treatment of said patient. Said method comprises the steps as above, and comparing said relative amount of said cells as identified to a sample taken earlier or in parallel from the same mammal, and/or to a control sample. Based on the results as provided by the method(s) of the invention, the attending physician will be able to conclude on the immune status of the patient, and adjust a treatment of the underlying disease accordingly.

Preferably, said method is performed without a step of purifying and/or enriching cells, preferably in whole blood and/or non-trypsinized tissue, or any other biological sample potentially containing said follicular helper T cells as e.g. a sample for cell transfer into a patient.

Another preferred aspect of the method according to the present invention then relates to a method as above, further comprising formulating said follicular helper T cells as identified for transplantation into a patient. Pharmaceutical preparations for these purposes and methods for their production are performed according to methods known in the art of transplantation medicine.

Another preferred aspect of the method according to the present invention relates to an oligomer according to any of SEQ ID NOs: 2 to 4, or the amplicon according to SEQ ID NO: 1.

Yet another preferred aspect of the present invention then relates to a kit for identifying, quantifying, and/or monitoring follicular helper T cells in a mammal based on the analysis of the bisulfite accessibility of CpG positions in the gene region of LIF, comprising components for performing a method according to the present invention, in particular a kit comprising a) a bisulfite reagent, and b) materials for the analysis of the methylation status of CpG positions selected from the CpG positions in the region according to SEQ ID NOs: 5 and/or 1, such as an oligomer selected from the sequences according to SEQ ID NOs: 2 to 4.

The present invention also encompasses the use of oligomers or amplicon or a kit according to the present invention for identifying and/or for monitoring follicular T helper cells in a mammal as described herein.

As mentioned above, recently three new cytosine modifications were discovered. Therefore, it is expected that future scientific findings will correct epigenetic patterns of modification described in the past. These past patterns of cytosine modification encompass bisulfite convertible (non-methylated, non-modified) and non-convertible (methylated, modified) cytosine. Both termini need to be corrected, as described. According to the novel scientific findings (i) non-bisulfite convertible cytosine encompasses 5-methylcytosine (mC) and 5-hydroxymethylcytosine (hmC), and (ii) bisulfite convertible (i.e. the "bisulfite convertibility") cytosine encompasses 5-formylcytosine (fC), 5-carboxycytosine (cC), as well as non-modified cytosine.

Additionally, past inventions are based on (i) the ratio of bisulfite convertible cytosine to whole amount of chromatin (cell-type independent, 100% bisulfite convertible DNA locus) or (ii) on the ratio of bisulfite convertible cytosine (fC, cC, non-modified cytosine) to non-bisulfite convertible cytosine (hmC and mC). These ratios characterize cell type, cell differentiation, cell stage as well as pathological cell stages. Therefore, new techniques will result in novel, more specific ratios and might supplement current cell specific, cell state specific as well as pathological patterns of epigenetic modifications and therefore, define potential novel biomarkers. Novel ratios to be discovered as biomarkers can be defined as:

Biomarker Ratio=$a/b$ $a=\Sigma$ (C and/or mC and/or hmC and/or fC and/or cC)
$b=\Sigma$ (C and/or mC and/or hmC and/or fC and/or cC),
whereby a and b differs from each other by one to four kinds of modifications. Discovery of novel DNA modifications will enlarge this enumeration.

For the purpose of definition for the present application, "epigenetic modifications" in the DNA sequence is referred to by the terminology of (i) bisulfite convertible cytosine (5-formylcytosine, (fC) and/or 5-carboxycytosine (cC)) and (ii) non-bisulfite convertible cytosine ((including 5-methylcytosine (mC), 5-hydroxymethylcytosine, (hmC)). As both kinds of methylation, mC and hmC, are not bisulfite convertible, it is not possible to distinguish between these two. Likewise, fC, cC as well as non-modified cytosine are bisulfite convertible and can also not be distinguished from each other as well. The term "methylated" DNA encompasses mC as well as hmC. The term "non-methylated" DNA encompasses fC, cC, and non-modified DNA. It is expected that novel variants of DNA modifications will be discovered in future. Each type of modification will be either bisulfite convertible or not. However, since the present method reliably distinguishes between the two groups, these novel modifications will also be usable as markers.

Furthermore, apart from the modifications of DNA, also histones undergo posttranslational modifications that alter their interaction with DNA and nuclear proteins. Modifications include methylation, acetylation, phosphorylation, ubiquitination, sumoylation, citrullination, and ADP-ribosylation. The core of the histones H2A, H2B, and H3 can also be modified. Histone modifications act in diverse biological processes such as gene regulation, DNA repair, chromosome condensation (mitosis) and spermatogenesis (meiosis). Also for these modifications a specific pattern of modification is specific for different cell types, cell stages, differentiation status and such a pattern can be analyzed for bisulfite convertibility or similar methods in order to identify certain cells and cell stages. The present invention also encompasses a use of these modifications.

In summary, using the LIF genetic region and in particular the amplicon as described herein as a marker, the inventors very specifically identified, quantified and particularly differentiated follicular T helper cells, and in their relation to other cell types in a sample, for example to overall T-lymphocytes.

The invention will now be further described based on the following examples and with reference to the accompanying figures and the sequence listing, without being limited thereto. For the purposes of the present invention, all references as cited herein are incorporated by reference in their entireties. In the Figures and Sequences.

FIG. 3 shows SEQ ID NO: 5 according to the present invention, with the amplicon AMP2305 according to the present invention indicated in bold, and the relevant CpG motifs underlined.

Figure 1:
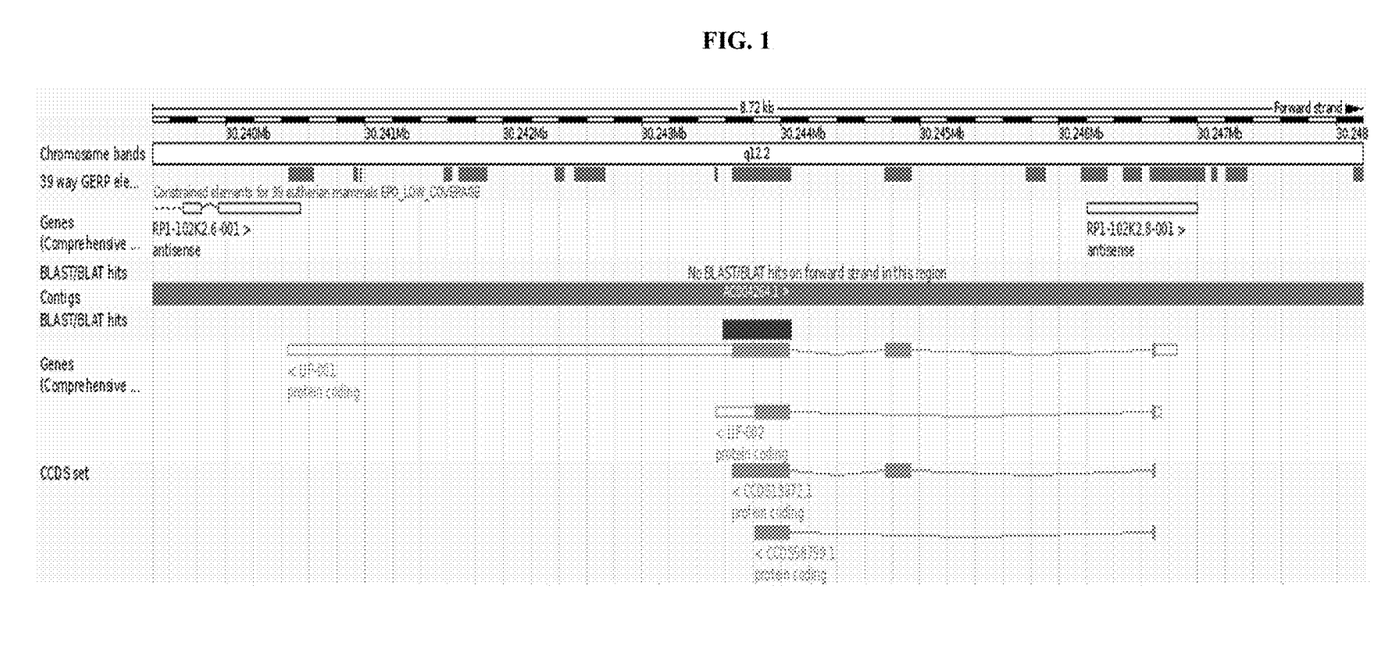
FIG. 1 shows the chromosomal location of the gene LIF (leukemia inhibitory factor)-ENSG00000128342 on chromosome 22: 30,240,447-30,246,851 reverse strand and the location of the amplicon AMP2305 according to the invention in the genetic region of LIF.
Figure 2:
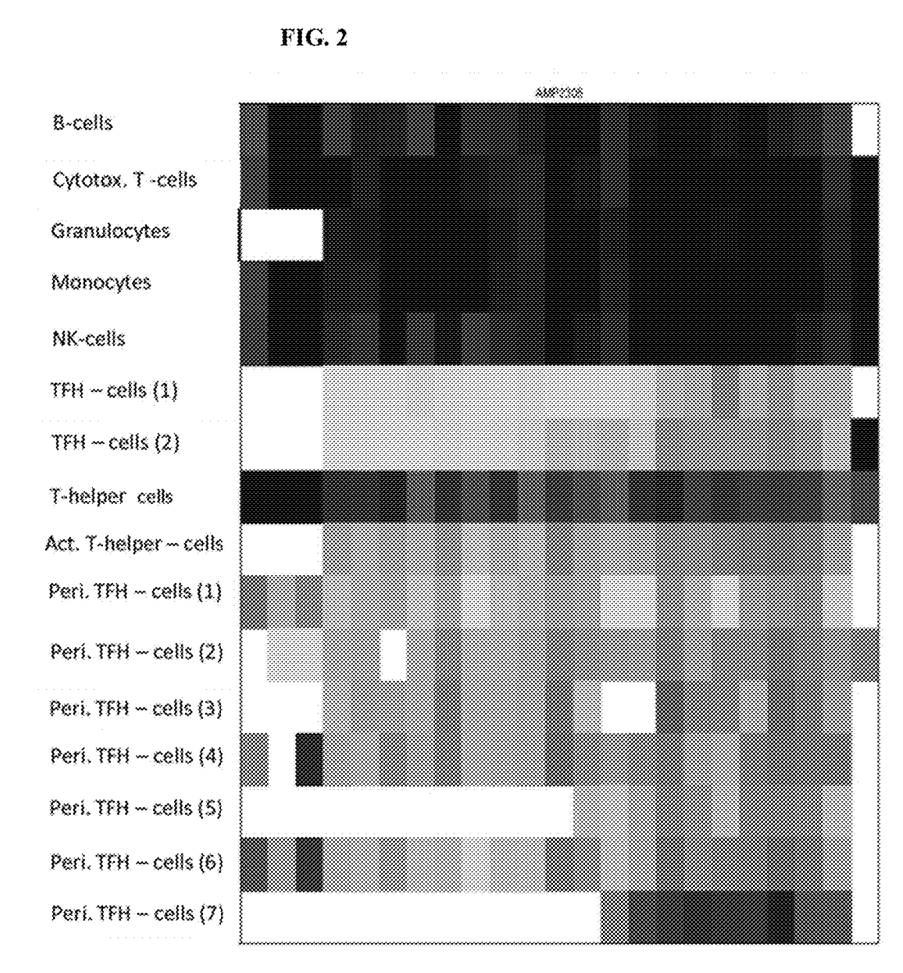
FIG. 2 shows the analysis of CpG sites on amplicon No. 2305 according to the invention. The horizontal boxes in the table correspond to the CpG positions in the amplicon as analyzed (e.g. CpG 1, 2, etc.), and the columns correspond to the cell types as analyzed. The abbreviations at the bottom indicate cytotox.=cytotoxic; Act. T helper cells=activated helper T cells; or (peri.) TFH=(peripheral) follicular helper T cells, respectively.

SEQ ID NO: 1 shows the genomic sequence of amplicon AMP2305 according to the present invention.

SEQ ID NO: 2 to SEQ ID NO: 4 show the sequences of specific oligomers according to the present invention.

SEQ ID NO: 5 shows the genomic sequence of the region of interest according to the present invention, with the about 2200 bases upstream of amplicon AMP2305, and the about 2600 bases downstream.

EXAMPLES

Example 1

In order to identify TFH-cells (follicular helper T cells), qPCR was performed on bisulphite converted samples stemming from the human genomic region according to the following sequence (AMP2305, SEQ ID NO: 1):

```
CTTCTGCCCCTCAGTACACAGCCCAGGGGAGCCGTTCCCCAACAACCTG

GACAAGCTATGTGGCCCCAACGTGACGGACTTCCCGCCCTTCCACGCCAA

CGGCACGGAGAAGGCCAAGCTGGTGGAGCTGTACCGCATAGTCGTGTACC

TTGGCACCTCCCTGGGCAACATCACCCGGGACCAGAAGATCCTCAACCCC

AGTGCCCTCAGCCTCCACAGCAAGCTCAACGCCACCGCCGACATCCTGCG

AGGCCTCCTTAGCAACGTGCTGTGCCGCCTGTGCAGCAAGTACCACGTGG

GCCATGTGGACGTGACCTACGGCCCTGACACCTCGGGTAAGGATGTCTTC

CAGAAGAAGAAGCTGGGCTGTCAACTCCTGGGGAAGTATAAGCAGATCAT

CGCCGTGTTGGCCCAGGCCTTCTAGCAGGAGGTCTTGAAGTGTGCTGTGA

ACCGAGGGATCTCAGGAGTTGGGTCCAGATGTGGGGGCCTGTCCAA
```

The following primers and probe were used for the qPCR:

```
Forward Primer
                                       (SEQ ID NO: 2)
q2305_TFH_fw      GTTTAATGTTATTGTTGATATTTTGT Reverse Primer
                                       (SEQ ID NO: 3)
q2305_TFH_rev     ACATCCACATAACCCACA Probe
                                       (SEQ ID NO: 4)
q2305_TFH_P_nm    TGTGTTGTGTTGTTTGTGTAGTAAGTATTAT
```

The cell type specificity (as measured by qPCR) was found as follows:

| Immune blood cell type | FACS characterization | Tissue | Percentage of TFH cells (%) |
|---|---|---|---|
| TFH06 (control) | CD3+, CD4+ CD45RA-, PD1++, CXCR5+ | tonsil | 95.03 |
| activated T helper cells | CD4+ CD69+, PD1- (TFH-) | tonsil | 85.39 |
| activated cytotoxic T cells | CD8+ CD69+, PD1- (TFH-) | tonsil | 15.84 |
| pTFH01 (peri. TFH) | | Peripheral blood | 94.79 |
| pTFH02 (peri. TFH) | | Peripheral blood | 74.91 |
| pTFH03 (peri. TFH) | | Peripheral blood | 73.82 |
| pTFH04 (peri. TFH) | | Peripheral blood | 73.95 |
| pTFH05 (peri. TFH) | | Peripheral blood | 91.81 |
| pTFH06 (peri. TFH) | | Peripheral blood | 90.23 |
| Granulocytes | CD15+ | Peripheral blood | 0.01 |
| Total cytotoxic T-cells | CD3+, CD8+ | Peripheral blood | 0.83 |
| Total T helper cells | CD3+, CD4+ | Peripheral blood | 23.41 |
| NK cells | CD3-, CD56+ | Peripheral blood | 0.53 |
| monocytes | CD14+ | Peripheral blood | 0.00 |
| Naïve CD4+ cells | CD4+, CD45RA+, CCR7+ | Periphery | 0.12 |
| Terminal differential effector memory CD4+ cells | CD4+, CD45RA+, CCR7- | Periphery | 62.94 |
| central memory CD4+ cells | CD4+, CD45RA-, CCR7+ | Periphery | 26.65 |
| effector memory CD4+ cells | CD4+, CD45RA-, CCR7- | Periphery | 57.18 |

In whole blood qPCR measurements, the following amount of TFH cells was determined/quantified. The samples are peripheral whole blood of an overall of 11 different (healthy) donors:

| Sample | Copy number TFH demethylated (LIF, SEQ ID NO: 1) | Copy number TFH methylated (LIF, SEQ ID NO: 1) | TFH cells (%) |
|---|---|---|---|
| 1 | 351.0 | 15166.7 | 2.26 |
| 2 | 260.7 | 16300.0 | 1.57 |
| 3 | 209.0 | 6680.0 | 3.03 |
| 4 | 234.7 | 11400.0 | 2.02 |
| 5 | 645.3 | 16500.0 | 3.76 |
| 6 | 462.7 | 14133.3 | 3.17 |
| 7 | 520.0 | 13633.3 | 3.67 |
| 8 | 595.7 | 12800.0 | 4.45 |
| 9 | 401.0 | 16600.0 | 2.36 |
| 10 | 339.7 | 14066.7 | 2.36 |
| 11 | 249.3 | 14500.0 | 1.69 |
| Mean value | | | 2.78 |

As similar analysis is made using the CpG positions as found within about 2200 bases upstream and/or within about 2600 bases downstream of amplicon AMP2305 (see SEQ ID NO: 5), whereby additional informative CpG positions are identified.

The invention claimed is:

1. A method for producing and detecting an amplicon from a bisulfite treated human leukemia inhibitory factor (LIF) gene region from human follicular helper T cells or activated helper T cells, the method comprising:
   a) bisulfite treating isolated DNA from a human T cell sample comprising the human follicular helper T cells or activated helper T cells to thereby generate bisulfite treated DNA where unmethylated cytosines are converted to uracils,
   b) producing the amplicon from the bisulfite treated DNA by amplifying with quantitative polymerase chain reaction (qPCR) a region of the bisulfite treated DNA comprising SEQ ID NO: 1 and having bisulfite convertible cytosine at one or more cytosine-phosphate-guanine (CpG) positions in SEQ ID NO: 1 prior to bisulfite treatment, and
   c) detecting the amplicon with a probe comprising the nucleic acid sequence of SEQ ID NO: 4.

2. The method according to claim 1, wherein said at least one CpG position is present in the 5' region upstream from a transcription start, promoter region, the 5' or 3' untranslated regions, exon, intron, exon/intron border and/or in the 3' region downstream of a transcriptional stop of said gene.

3. The method according to claim 1, wherein the CpG position corresponds to any one of CpG positions in SEQ ID NO: 1.

4. The method according to claim 1, further comprising detecting the bisulfite convertible cytosine using a method selected from a methylation specific enzymatic digest; bisulfite sequencing; an analysis selected from promoter methylation, CpG island methylation, MSP, HeavyMethyl, MethyLight, and Ms-SNuPE; and other methods relying on a detection of amplified DNA.

5. The method according to claim 1, wherein said sample is a body fluid, tissue, organ, or cell.

6. The method according to claim 1, wherein said method is performed without a step of purifying and/or enriching said cells.

7. The method according to claim 1, wherein said sample is from a subject suffering from or is likely to suffer from an autoimmune disease, transplant rejection, infection, cancer, and/or an allergy.

8. The method of claim 1 performed using a kit, comprising a) a bisulfite reagent, and b) materials for detecting the bisulfite convertible cytosine at the at least one CpG position.

9. The method according to claim 1, wherein the amplifying comprises using an oligomer comprising a nucleic acid sequence of any of SEQ ID NOs: 2 to 4.

10. The method according to claim 3, wherein the CpG position is selected from CpG positions 1, 2, 3, 4, 5, 6, 7, 8, 9, 10, 11, 12, 13, 14, 15, 16, 17, 18, 19, 20, 21, 22, and 23 of SEQ ID NO: 1.

11. The method, according to claim 5, wherein the sample is a blood sample.

12. The method, according to claim 5, wherein the sample is whole blood and/or non-trypsonized tissue.

13. The method according to claim 8, wherein the materials for detecting the bisulfite convertible cytosine comprise an oligo selected from the sequences according to SEQ ID NOs: 2 to 4.

14. The method according to claim 1, wherein the human T cell sample is isolated from a human blood sample.

15. The method of claim 1, comprising
   d) detecting methylation status of the one or more cytosine-phosphate-guanine (CpG) positions from the amplicon.

16. The method of claim 1, wherein the qPCR is performed with methylation specific primers.

17. The method of claim 1, wherein the one or more CpG positions comprising the bisulfite convertible cytosine is selected from CpG positions 3, 4, 5, 6, 7, 8, 9, 10, 11, 12, 13, 14, 15, 16, 17, 18, 19, 20, and 21 in SEQ ID NO: 1.

18. The method of claim 1, wherein SEQ ID NO: 1 comprises a bisulfite convertible cytosine at CpG positions 11, 12, 13, 14, 15, 16, 17, 18, and 19 relative to SEQ ID NO: 1.

* * * * *

SEQUENCE LISTING

<160> NUMBER OF SEQ ID NOS: 5

<210> SEQ ID NO 1
<211> LENGTH: 496
<212> TYPE: DNA
<213> ORGANISM: Homo sapiens

<400> SEQUENCE: 1

```
cttctgcccc tcagtacaca gcccaggggg agccgttccc caacaacctg gacaagctat      60
gtggccccaa cgtgacggac ttcccgccct tccacgccaa cggcacggag aaggccaagc     120
tggtggagct gtaccgcata gtcgtgtacc ttggcacctc cctgggcaac atcacccggg     180
accagaagat cctcaacccc agtgccctca gcctccacag caagctcaac gccaccgccg     240
acatcctgcg aggcctcctt agcaacgtgc tgtgccgcct gtgcagcaag taccacgtgg     300
```

| | |
|---|---|
| gccatgtgga cgtgacctac ggccctgaca cctcgggtaa ggatgtcttc cagaagaaga | 360 |
| agctgggctg tcaactcctg gggaagtata agcagatcat cgccgtgttg gcccaggcct | 420 |
| tctagcagga ggtcttgaag tgtgctgtga accgagggat ctcaggagtt gggtccagat | 480 |
| gtgggggcct gtccaa | 496 |

```
<210> SEQ ID NO 2
<211> LENGTH: 26
<212> TYPE: DNA
<213> ORGANISM: Homo sapiens

<400> SEQUENCE: 2
```

| | |
|---|---|
| gtttaatgtt attgttgata ttttgt | 26 |

```
<210> SEQ ID NO 3
<211> LENGTH: 18
<212> TYPE: DNA
<213> ORGANISM: Homo sapiens

<400> SEQUENCE: 3
```

| | |
|---|---|
| acatccacat aacccaca | 18 |

```
<210> SEQ ID NO 4
<211> LENGTH: 31
<212> TYPE: DNA
<213> ORGANISM: homo sapiens

<400> SEQUENCE: 4
```

| | |
|---|---|
| tgtgttgtgt tgtttgtgta gtaagtatta t | 31 |

```
<210> SEQ ID NO 5
<211> LENGTH: 5531
<212> TYPE: DNA
<213> ORGANISM: homo sapiens

<400> SEQUENCE: 5
```

| | |
|---|---|
| ctgaggatgg gtcccatggg gccaagtcca ggctgggtgg gagagcgact cagagccagg | 60 |
| gccgcaaggt gggcctggca cagagctccc aagtccacag ggagatgagg tgatgggcga | 120 |
| gtcagccggg ccccccgggt ggaatcagca actctggttt ccagacaagt tgtctttct | 180 |
| cgaagcccat cctgggggaa tgcagccagc cccaagctaa gccggatgaa gcaggaagga | 240 |
| gaaggcagtc cctgcatcct ggacaagggt gagtgtggcc cacatctcaa cagccacatc | 300 |
| ctcgtcttgc tgttgggatg gacagatgga caactccggg ccgcaccctc caccccaacc | 360 |
| ccaggcctca ggacctgcct gcacactgcc cacgcgccat ccaggtaaag tgcttagaga | 420 |
| gcgacaggga aaggtgcaaa gtgagtgaaa agtaccataa ttagtaccat catcttgtcg | 480 |
| gaggaacttg gaggccggca gccgctcag ggtttgagaa gaagccagaa cactgctctg | 540 |
| agcagctgcc ccaactctgc tgcctccttc cctcccctgc tctcagactg gagggcgttt | 600 |
| ctccactcgc ctggccccag cacaaaggaa gagatcgggt tccctgcctg ggagcccaga | 660 |
| catgggtggg agtgggatgg gggtggagca ggagggccca cagcttcctg gtctgagtcc | 720 |
| caggcatctg cagcctccct ctcctcctct tgggagcaat gggcagctga tcccccagt | 780 |
| ctaccccacc ttcctggggt ctggcccagc caggcccccc gcaccgtcta tgggtgtccg | 840 |
| ggccacagga ggagcttccc tgctgtgtcg gagcatgctg ggtgcagggg cagggttgtt | 900 |
| ccagggcgct atttcagagg cagcatgggg acacagaaac aaggacaggg tgggccacaa | 960 |
| ggactgtctt gcccactgct ccaggggggca caatatctgc caggaacagt gcgcctcaca | 1020 |

```
acacaatgct ggggcgccca agaacagtgt gaaccagccc cctggaatca agacagaaag    1080
gcacccggcc tctccacaaa ttggcccagc ccctgcagcc tggaccctga caccctaaag    1140
caagtcacag taggggatgg ggggggggtgg agcaaggccc cccactccca ctcaggcctc    1200
cccattctct cagatccgac ccttctctga gcttcacccg taaggcttat tccacttgta    1260
acattgtcga cttccagacc aggccctgct aagccctggc cctggcgctt gtgtcgggag    1320
ccatcatcat attttgttga gtagggacca gggaaagggg aattaacttg gccactgaaa    1380
gcaccaataa gttaatataa ataggatatc ataataaata gaaatcatgc caggtcagac    1440
gcacagcacg cttggagctc agggttccct gagaccctga ccctaagttc tgctgttccc    1500
ttgccctggg gaccagagac ggcctccagt cccccctcaag tacctctgtg tgacctcaca    1560
aggcctccca gggcctcaga tgtgagctgc tactctgagc taccccagcc ccttcttaca    1620
gacctttacc cagaggaaga gcctgggtcc ctcagaacct ctgcacctga cttagcaacc    1680
tgcccctgcc ctaccacct ccacaaaccc ctgctgcagg tccagccatc agaccctggc    1740
catcccaggc tgcagggaag atcacgggga agagaacgaa gaacctacca aagctttcca    1800
ggcctctcct cctcccagtg tcttccttcc caggcctgaa ggtggcttct ctgcctcccc    1860
aagagcctga atgccaagtg acctccttct ggaaacttct gccagattgt tcctatgccc    1920
aagttctctg atcatcctca aaagaagaca gccttccatc ccagaggccc ctctctatct    1980
tccactcatc aaacttctag gggacaagga gtcctttggg atcctagccc ctctggccca    2040
cctaagtccc aacctaaggg gcagcaaagg cacagatggt gataatttgc tgggggctgg    2100
tccactcccc tgggccctgc tgtctcaccc tgtggtcagg gctcttgtag atgacttgtg    2160
tagtttgttc actgcacaaa gtgagcaagg ggccaaaggg acaagtagag gcagaagtcc    2220
agcccacgct ccccagtcca caatctccca gaggaagggg caccttcttc tagctccctc    2280
cctatggaag tttccactct gctcagcttc atcacagccc agcccagagt ggagtggact    2340
ggccaggcac cctcggggtc tgccagcagc ccccatttgg gtttagcgat gccctgggcc    2400
ccagccaccc ttggacaggc ccccacatct ggacccaact cctgagatcc ctcggttcac    2460
agcacacttc aagacctcct gctagaaggc ctgggccaac acggcgatga tctgcttata    2520
cttccccagg agttgacagc ccagcttctt cttctggaag acatccttac ccgaggtgtc    2580
agggccgtag gtcacgtcca catggcccac gtggtacttg ctgcacaggc ggcacagcac    2640
gttgctaagg aggcctcgca ggatgtcggc ggtggcgttg agcttgctgt ggaggctgag    2700
ggcactgggg ttgaggatct tctggtcccg ggtgatgttg cccagggagg tgccaaggta    2760
cacgactatg cggtacagct ccaccagctt ggccttctcc gtgccgttgg cgtggaaggg    2820
cgggaagtcc gtcacgttgg ggccacatag cttgtccagg ttgttgggga acggctcccc    2880
ctgggctgtg tactgagggg cagaagggag gtgacgtggg agtcaggggt cagtgtccca    2940
gccctgccgc caacccttg gcaagctct tgcgtctgtt tccccatcta gcgcatgagg    3000
acccaactcc ttgccctgta agcatctgga attgtcatga gagccaaaac taattgtaat    3060
gtgagtgccc ttgctaaaga tcaaagactg agccatgcac gcagtcatca ttatcatcat    3120
catcatcatc accaccctaa ggggacagaa gggaaaactc ggtgtctagc cctagctggg    3180
gcaccacaca caagtacttc catccctgca ctcacaatgt tccgggacgc ccctccatgc    3240
ccagcaccca cagcccactg cctctcaacc gcatctccct ggtgcctcac gcccatttcc    3300
cctccatccc tcgctccctg cagcaggaca atcacaagat aagaagtgcc aggtccccac    3360
```

```
ctttgcactc agttctcccc ttgctaactg ggcaccctgg ggaagcttcc ctggggaagc      3420
ttgggcagga agtggcggga gtctgggggt ggtttaatca agccctctcc ccattctctc      3480
cttccagccc caaaaggtcc cctcaaccca gatcaggaca gccnctaatg atatttacaa      3540
gcccnctccc tgccatctcc tgtcagtatc ccaggggtaa cttacataga gaataaagag      3600
ggcattggca ctgccattga gctgtgccag ttggctcctg atctggttca tgaggttgtt      3660
gtgacatggg tggcgtatgg cacaggtggc gttgacaggg gtgatgggga ggggctccc      3720 cgccccatgt ttccagtgca gaaccaacag caggggcaca actcctgggg acagtcagga      3780
agaagccatg agtagaaagg caggaaaggg tggcctgggg tcatggcaca ccggatgggg      3840
gtccaacaat ggccgcatgg gagaggactc ctggttcccc ctcaccacct gcagctgtct      3900
tcctggggcc tagtcttcac tctgtcactg cgtgtgtttc tctgtctccc tttctctacc      3960
ttagttctcc ctgctctctt ctgggatgac gtaaagatga gggcaagaca caagccattt      4020
ccacccaaag ggtgcagggt ccaggagaga ctcccagcca tcccacccct tccctcagga      4080
aggcaaaggt cctaaggccc cctggccctc tggctggaag gcaccaggcc ccaggcccag      4140
caggcaccag gagaaaggag acccctctct tcccacctcc cgtggtggcc caggttcctc      4200
agcagcgctt cccactcact ggcccattgc agcccaaatc tccgaagcca ggcacccatg      4260
ggggccacgg ggcatggggg agtggggagg agtcctcggt tgaccctcat ctccctccca      4320
aacctgccac ttgattctgg ctccctgggc caattgcccc caattctgcc cccgccccca      4380
tcatcctcta tctcttcctt ccctagtgtc ccctatctca ctcaagctca ccccatttct      4440
gcctggctgt ccccactctc catccccaaa tcatcattca aaactctctg ttcccccagc      4500
tccggacagc ccctgactcc atgccttctc ccgactcatc cgctgtccct tgtcccaggg      4560
gttcccctcc ctcctaacac acacacaccg gctcagggag ggagaggaaa tggtgcacca      4620
ggagagagaa aaggcaaaag gtcataggca gtcgggtggg cggggaggaa ggaaagtgaa      4680
aggtgacagg agagctggga gctgtcccga catgtcctgg tttgccnctc ccccaggggg      4740
gcctgttctc ccgactcccc ccaggccccc ttagacgctt ttccagggct ctgcagaagg      4800
gcacctgaag atggtggggg ccggggtcag cgggcgagtg aggctggaga cctcccccgg      4860
atccnccatg ctggaacagc ggggacaggg gcctcctcaa gttcacttct cctgggtccc      4920
ctgttcgtcc cagcatccca aggcagtgct gaggcccngg ggtggctgcg ggagggggc      4980 cacaccccta tatctcacct agcgcagacc acacgcttcc agacaccagc agatggaggc      5040
ggcacctgct cccgtcccag gccggagttt gcaagctgct cgccgcccgc gcccctccct      5100
gggagcagcc cggaccgcg gttggaaagg agaaagcgga agaaagaaa gaaaagaaaa      5160 agagagaggg agagtgaatc tgggagaaag cgcagaggga gagcagcca gcgagtgtcc      5220 ggagcgagga ggaggaggag gagaaggaga ggggaagaa gaggaggagg aggaaggctc      5280
ggcgccccct ccctcgccgc caacctgccg cggggcgtgc ggtgcttggg accatgtgcc      5340
cgcgctcgct ccgggccgcc acccagcgcc tccggtggct gcgcgggcgc cccaagtgtt      5400
cgtgtgtctg cggcgggtgg gcgtccggct cgcgctgcca agcgccccaa gttgccgccg      5460
cgccccgcag cggggacgcg aagccggcgc ggggcgggtg tatttacctg ccgccaagac      5520
cttcattatg g                                                          5531
```